United States Patent [19]

Beltramini et al.

[11] Patent Number: 4,780,400
[45] Date of Patent: Oct. 25, 1988

[54] SILVER HALIDE EMULSION CONTAINING A 2-UNSUBSTITUTED N-ALKENYL-THIAZOLIUM SALT AS LATENT IMAGE STABILIZER AND PHOTOGRAPHIC ELEMENTS INCLUDING SAID EMULSION

[75] Inventors: Walter Beltramini, Savona; Francesco Squarcia, Bologna, both of Italy

[73] Assignee: Minnesota Mining and Manufacturing Company, St. Paul, Minn.

[21] Appl. No.: 40,284

[22] Filed: Apr. 20, 1987

[30] Foreign Application Priority Data

Apr. 28, 1986 [IT] Italy ................................ 20238 A/86

[51] Int. Cl.$^4$ .............................................. G03C 1/34
[52] U.S. Cl. ........................................ 430/505; 430/614
[58] Field of Search ................................ 430/614, 505

[56] References Cited

U.S. PATENT DOCUMENTS

| 3,954,478 | 5/1976 | Arai et al. | 96/100 |
| 4,423,140 | 12/1983 | Herz | 430/611 |
| 4,451,557 | 5/1984 | Lok et al. | 430/614 |

FOREIGN PATENT DOCUMENTS 522997 7/1940 United Kingdom .
656942 9/1951 United Kingdom .

*Primary Examiner*—Won H. Louie
*Attorney, Agent, or Firm*—Donald M. Sell; Mark A. Litman

[57] ABSTRACT

Silver halide light-sensitive emulsions are protected against latent image fading by an effective amount of a 2-unsubstituted N-alkenyl-thiazolium salt compound.

16 Claims, No Drawings

SILVER HALIDE EMULSION CONTAINING A 2-UNSUBSTITUTED N-ALKENYL-THIAZOLIUM SALT AS LATENT IMAGE STABILIZER AND PHOTOGRAPHIC ELEMENTS INCLUDING SAID EMULSION

BACKGROUND OF THE INVENTION

1. Field of the Invention

The present invention relates to photographic silver halide emulsions stabilized against latent image fading and to photographic elements including such emulsions especially for use in color photography.

2. Description of the Prior Art

It is known in the art that obtaining of photographic images by exposure and development of a photographic element may be negatively effected by fading of the latent image. It has been described in U.S. Pat. No. 3,954,478 that certain benzothiazolium salt compounds, previously known in the art as antifoggants (see German Pat. No. 867,355) are particularly useful as latent image stabilizers. It has been described in U.S. Pat. No. 4,423,140 that certain compounds, which are obtained by alkaline hydrolysis of said compounds, are more effective than the benzothiazolium salt compounds of U.S. Pat. No. 3,954,478. It has been described in U.S. Pat. No. 4,374,196 that the hydrolysis products of certain thiazolium salt compounds are active as latent image stabilizers, while the salt compounds are not.

All of the benzothiazolium and thiazolium salt compounds and their hydrolysis products described in such patents as latent image stabilizers include an N-alkenyl substituent (described for the first time in German Patent 867,355), which appear to be sufficient to impart latent image stabilizing properties to the benzothiazolium salt compounds but not to the thiazolium salt compounds.

SUMMARY OF THE INVENTION

It has been found that a 2-unsubstituted N-alkenyl thiazolium salt compound is effective as a latent image stabilizer in a photographic silver halide emulsion without showing significant adverse effects on the developability of color photographic elements including an emulsion stabilized with said compound.

DETAILED DESCRIPTION OF THE INVENTION

The present invention relates to a photographic silver halide emulsion containing a latent image stabilizing amount of a 2-unsubstituted N-alkenyl-thiazolium salt compound. Such compound can be described by the following formula (I):

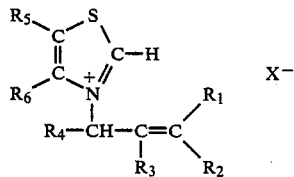

wherein $X^-$ represents an anion and $R_1$, $R_2$, $R_3$, $R_4$, $R_5$ and $R_6$ each represent hydrogen or any photographically compatible substituent. These substituents are well-known in the art and are selected upon the basis of various common criteria. For example they should be reasonable in size and nature, useful to the properties of the compounds such as, for example, to control the solubility in neutral, acid or alkaline water solutions and to control the solubility of the product and the stability of its complexes with silver to obtain the desired stabilizing effects without any significant deleterious effects on the photographic characteristics of the emulsion such as fog, sensitivity and contrast.

It is believed that the unsubstituted N-allylthiazolium salt compounds of the invention are the most economical and simple to use stabilizing agents of the invention which enable very good latent image stability with no significant loss of the developability of the silver halide emulsion. The skilled in the art may use substituted compounds which are chosen on the basis of known criteria used to adapt the compounds to particular needs.

In the compounds represented by the formula (I) above, $X^-$ preferably represents an acid anion (e.g., chloride, bromide, iodide, thiocyanate, methylsulfate, ethylsulfate, perchlorate, p-toluenesulfonate ions and other well-known photographically inert or harmless anions); $R_1$, $R_2$, $R_3$ and $R_4$ each preferably represent a hydrogen atom or an alkyl group; $R_5$ and $R_6$ each preferably represent a hydrogen atom, an alkyl group, an alkoxy group, an electron withdrawing group or can combine to form a 5- and 6-membered non-aromatic ring; examples of electron withdrawing groups include an aryl group, a cyano group, a halogen atom, a carboxy group, an alkylcarbonyl group, an arylcarbonyl group, an alkoxycarbonyl group, an aryloxycarbonyl group or an aminocarbonyl group. Sulfonyl and phosphonyl counterparts of the carbonyls would also be useful.

The alkyl groups and the alkyl portions of the alkoxy groups, of the alkylcarbonyl groups and of the alkoxycarbonyl groups preferably contain 1 to 8 carbon atoms, and most preferably contain 1 to 4 carbon atoms (e.g., methyl, ethyl, propyl, iso-propyl, butyl, iso-butyl, tertiarybutyl), and include substituted and unsubstituted groups.

The aryl groups and the aryl portions of the arylcarbonyl and aryloxycarbonyl groups preferably contain 6 to 10 ring carbon atoms (e.g., phenyl, naphthyl) and include substituted and unsubstituted groups.

The 5- and 6-membered non-aromatic ring includes monocyclic unsaturated hydrocarbons (e.g., cyclopentene, cyclopentadiene, cyclohexene, cyclohexadiene) and includes substituted and unsubstituted rings.

The 2-unsubstituted N-alkenylthiazolium salt can be prepared by reacting a corresponding 2-unsubstituted N-alkenylthiazole compound with an alkenyl halide.

Typical examples of N-alkenyl-thiazolium salts of the present invention include:

(1) N-allyl-thiazolium bromide
(2) N-allyl-thiazolium chloride
(3) N-allyl-thiazolium iodide
(4) N-allyl-4-methyl-thiazolium bromide
(5) N-allyl-4,5-dimethyl-thiazolium bromide
(6) N-allyl-4-methoxy-thiazolium bromide
(7) N-allyl-4-methoxy-5-methyl-thiazolium bromide
(8) N-allyl-4-(β-hydroxy)-ethyl-5-methyl-thiazolium bromide
(9) N-2-butenyl-thiazolium bromide
(10) N-(2-methyl)-allyl-thiazolium bromide
(11) N-allyl-5-chloro-thiazolium bromide.

The latent image stabilizing compounds of the present invention are preferably incorporated in the silver halide emulsion. They can be added to the silver halide emulsions at any point after the formation of the silver halide grains, preferably after chemical and spectral sensitization, but before coating of the emulsion on the support, so that they can interact with the grains prior to exposure.

The most useful amount of the latent image stabilizing compounds of the present invention varies correspondingly with such factors, such as the silver halide composition, the nature of the other components of the emulsion, the use of the photographic element, and the like. However, useful amounts are in the range from about 0.01 to about 50 millimole per mole of silver and preferably from about 0.1 to about 10 millimole per mole of silver.

Accordingly, the present invention relates to a photographic silver halide emulsion containing a latent image stabilizing amount of a compound as described above. Further, the present invention relates to a photographic element comprising a support base bearing a layer of a silver halide emulsion containing a stabilizing amount of a compound as described above.

The silver halide emulsions used in the present invention can be any of the silver halide emulsions known in the art such as silver chloride, silver bromide, silver bromo-chloride, silver chloro-iodide, silver bromo-iodide, silver chloro-bromo-iodide emulsions and mixtures thereof. The emulsions can be composed of coarse, medium and fine grains and can be monodispersed or polydispersed. The silver halide grains may be those having a regular crystal form, such as a cube or an octahedron, or those having an irregular crystal form, such as a sphere or tablet, etc., or may be those having a composite crystal form (e.g., epitaxial growth). They may be composed of a mixture of grains having different crystal forms. Their size can be varied on a wide range, but in general average grain sizes from 0.1 to 4 $\mu$ are suitable.

The silver halide emulsions used in the present invention may be obtained according to any of the known acid, neutral and ammoniacal method using conventional precipitation methods such as a single or twin jet method. Further, the silver halide emulsions may be chemically sensitized with a sulfur sensitizer, such as allylthiocarbamide, thiourea, cystine, etc.; and active or inert selenium sensitizer; a reducing sensitizer such as stannous salt, a polyamine, etc; a noble metal sensitizer, such as gold sensitizer, more specifically potassium aurithiocyanate, potassium chloroaurate, etc.; or a sensitizer of a water soluble salt such as for instance of ruthenium, rhodium, iridium and the like, more specifically, ammonium chloropalladate, potassium chloroplatinate and sodium chloropalladite, etc.; each beng employed either singly or in a suitable combination.

Furthermore, the above silver halide emulsions may contain various known additives for photography. For example, there may be employed additives for photography as disclosed in Research Disclosure, Item 17643, December 1978.

Further, the silver halides may be optically sensitized to a desired wavelength region. The method for spectral sensitization of the present invention is not particularly limited. For example, optical sensitization may be possible by using an optical sensitizer, including a cyanine dye, a merocyanine dye, complex cyanine and merocyanine dyes, oxonol dyes, hemioxonol dyes, styryl dyes and streptocyanine dyes, either singly or in combination. Particularly useful optical sensitizers are the dyes of the benzoxazole, benzimidazole and benzothiazole carbocyanine type.

The above emulsions may also contain various additives conveniently used depending to their purpose. These additives include, for example, stabilizers or antifoggants such as azaindenes, triazoles, tetrazoles, imidazolium salts, polyhydroxy compounds and others; film hardeners such as of aldehyde type, aziridine type, isoxazole type, vinylsulfone type, acryloyl type, triazine type, etc.; developing promoters such as benzyl alcohol, polyoxyethylene type compounds,etc.; image stabilizers such as of chromane type, cumarane type, bisphenol type, etc.; and lubricants such as wax, glycerides of higher fatty acids, higher alcohol esters of higher fatty acids, etc. Also, coating aids, modifiers of the permeability in the processing liquids, defoaming agents, antistatic agents and matting agents may be used. As hydrophilic colloids to be used in the emulsion according to the present invention, not only gelatin but also gelatin derivatives, polymer grafts of gelatin, synthetic hydrophilic macromolecular substances and natural hydrophilic macromolecular substances other than gelatin may also be available either as a single species or in a mixture. Also, synthetic latexes may be added to gelatin to improve the film properties such as copolymers of acrylic acid esters, vinyl esters, etc. with other monomers having ethylenic groups.

As the support for the light-sensitive element, there may be used, for example, baryta paper, polyethylene-coated paper, polypropylene synthetic paper, cellulose acetate, polystyrene, a polyester film such as polyethyleneterephthalate, etc. These supports may be chosen depending on the purpose of use of the light-sensitive silver halide photographic material. The supports may be provided with a subbing layer, if necessary.

The photographic emulsions of the present invention can be used for black-and-white light-sensitive negative elements, light-sensitive positive elements, X-ray elements, photothermographic elements, lithographic elements, black-and-white and color light-sensitive elements for diffusion transfer processes and light-sensitive elements which contain oil-soluble or water-soluble color couplers.

Preferably, the silver halide emulsions according to the present invention can be designed for multicolor elements comprising dye image forming units sensitive to each of the three primary regions (blue, green and red) of the visible spectrum. Each unit can be formed by a single emulsion layer or multiple emulsion layers sensitive to the same spectral region.

More preferably, the silver halide emulsions according to the present invention can be designed for multicolor element comprising a support bearing at least one blue-sensitive silver halide emulsion layer and preferably two blue-sensitive silver halide emulsion layers of different sensitivity associated to yellow dye forming couplers, at least one green sensitive silver halide emulsion layer and preferably at least two green-sensitive silver halide emulsion layers of different sensitivity associated to magenta dye forming couplers, and at least one red-sensitive silver halide emulsion layer and preferably at least two red-sensitive silver halide emulsion layers of different sensitivity associated to cyan dye forming couplers, wherein at least one silver halide emulsion layer comprises a latent image stabilizing amount of a compound of the present invention.

As the yellow couplers, there may be employed, for example, the known open-chain ketomethylene type couplers. Among them, benzoylacetanilide type and pivaloylacetanilide type compounds are useful.

As the magenta couplers, there may be employed, for examle, pyrazolone type compounds, pyrazolotriazone type compounds, indazolone type compounds, cyanoacetyl type compounds. As the cyan couplers, for example, phenol type compounds and naphthol type compounds are useful.

The elements of the present invention can contain additional layers of common use in photographic elements such as protective layers, intermediate layers, filter layers, antihalation layers and the like. The following examples further illustrates the invention.

PREPARATIVE EXAMPLE 1

N-allylthiazolium bromide

This compound was prepared as follows:

Allyl bromide (7 ml.=0.084 mole) and thiazole (5 ml.=0.07 mole) were heated at 78° C. for 20 minutes under stirring.

Anhydrous toluene (20 ml) was then added and the separated solid was filtered and dried under vacuum, to give the N-allylthiazolium bromide (14 g., yield 97%).

The structure of the compound was confirmed by elemental analysis and nuclear magnetic resonance spectrum.

PREPARATIVE EXAMPLE 2

N-allyl-2,4-dimethylthiazolium bromide (Comparative Compound)

This compound was prepared as follows:

Allyl bromide (14.52 g.=0.12 mole) and 2,4-dimethylthiazole (11.32 g.=0.1 mole) were heated at 78° C. for 20 minutes under stirring.

Anhydrous toluene (140 ml) was added and the separated solid was filtered and dried under vacuum to give the N-allyl-2,4-dimethylthiazolium bromide (22 g., yield 95%). The structure of the compound was confirmed by elemental analysis and nuclear magnetic resonance spectrum.

PREPARATIVE EXAMPLE 3

N-allyl-5-chloro-thiazolium bromide

This compound was prepared as follows:

Allyl bromide (1.7 ml=0.02 mole) and 5- chloro-triazole (2.0 g=0.0167 mole), prepared according to Bull. Soc. France 1962, pages 1735–1738 in 47% yield, were heated at 78° C. for 30 minutes under stirring. The resulting solid was suspended in ethylether, filtered and dried to give N-allyl-5-chloro-thiazolium bromide (1.5 g, yield 37.5%).

| Empirical formula: $C_6H_7NBrClS$ | | | | |
|---|---|---|---|---|
| C % | H % | N % | Br % | S % |
| Calculated 29.95 | 2.93 | 5.82 | 33.22 | 13.33 |
| Found 30.10 | 2.96 | 5.75 | 33.18 | 13.29 |

EXAMPLE 1

A first photographic element (Element 1) was prepared having the following structure:

(a) Overcoat layer
(b) High speed blue-sensitive silver halide emulsion layer comprising:

a silver bromo-iodide emulsion having 11% mole iodide and average grain size of 0.75 μ coated at a coverage of 0.45 g Ag/m²;
gelatin at a coverage of 0.059 g/m²;
a yellow dye forming coupler at a coverage of 0.059 g/m²

(c) Low speed blue-sensitive silver halide emulsion layer comprising:

a silver bromo-iodide emulsion having 2,4% mole iodide and average grain size of 0.24μ and a silver bromo-chloro-iodide emulsion having 5% mole chloride and 7% mole iodide and average grain size of 0.48μ, blended at a weight ratio of 65:35 and coated at a total coverage of 1.0 g/m² of silver;
gelatin at a coverage of 2.33 g/m²;
a yellow dye forming coupler at a coverage of 1.904 g/m²

(d) Yellow filter layer
(e) High speed green-sensitive silver halide emulsion layer
(f) Low speed green-sensitive silver halide emulsion layer
(g) High speed red-sensitive silver halide emulsion layer
(h) Low speed red-sensitive silver halide emulsion layer
(i) Support base.

A second photographic element (Element 2) was prepared which was identical to Element 1 except that the high speed blue-sensitive silver halide emulsion layer contained 0.23 millimole/mole of silver of the latent image stabilizer prepared in the Preparative example 1 and the low speed blue-sensitive silver halide emulsion layer contained 0.5 millimole/mole of silver of the same stabilizer.

A third photographic element (Element 3) was prepared which was identical to Element 1 except that the high speed blue-sensitive silver halide emulsion layer contained the compound prepared in the Preparative example 2 and the low speed blue-sensitive silver halide emulsion layer contained the same compound; amounts of said compound were equivalent to those of the latent image stabilizer of Element 2.

Two samples (Sample 1 and 2) of each element were exposed at 5000° K. through a continuous wedge of 0.30 gradient. Other two samples (Sample 3 and 4) of each element were not exposed. Samples 1 and 3 of each element were stored in a freezer at −18° C., while samples 2 and 4 were stored at 24° C. and 50% relative humidity.

After four months of storing as described above, samples 3 and 4 of each element were exposed as said above, then all the samples (1, 2, 3 and 4 of each element, all exposed) were processed in a C-41 process as described in British Journal of Photography, July 1974, pages, 597–598.

The sensitometric results (fog and maximum density) and the relative speed of each sample, measured at 0.20 (Speed 1) above fog, are reported in the Table below.

In each element, the greater is the loss of relative speed of sample 2 with respect to samples 1 and 4, the greater is the amount of latent image fading; moreover, the greater the loss of speed of sample 4 with respect to sample 3, the greater the instability of the unexposed element.

TABLE 1

| Element | Sample | Fog | D. Max | Speed 1 |
|---|---|---|---|---|
| 1 | 4 | 0.76 | 3.31 | 91 |
| (Control) | 3 | 0.77 | 3.28 | 100 |

TABLE 1-continued

| Element | Sample | Fog | D. Max | Speed 1 |
|---|---|---|---|---|
| | 2 | 0.76 | 3.30 | 84 |
| | 1 | 0.77 | 3.29 | 99 |
| 2 | 4 | 0.78 | 3.35 | 105 |
| (Invention) | 3 | 0.78 | 3.29 | 105 |
| | 2 | 0.77 | 3.28 | 103 |
| | 1 | 0.78 | 3.30 | 104 |
| 3 | 4 | 0.78 | 3.27 | 97 |
| (Comparison) | 3 | 0.78 | 3.24 | 101 |
| | 2 | 0.78 | 3.29 | 88 |
| | 1 | 0.78 | 3.30 | 99 |

It can be understood from these results that the compound of the present invention has excellent effects in substantially inhibiting latent image fading and improving the stability of the unexposed element. Moreover, comparing the same samples of different elements, the element of the present invention has increased relative speed.

EXAMPLE 2

A new photographic element (Element 4) was prepared having the following structure:
(a) Support base;
(b) Yellow filter layer;
(c) The low-speed blue-sensitive silver halide emulsion layer of Example 1;
(d) Protective layer.

A second photographic element (Element 5) was prepared which was identical to Element 4 except that the blue-sensitive silver halide emulsion layer contained 0.4 millimole/mole of silver of the latent image stabilizer prepared according to Preparative Example 3.

Two samples (Sample 1 and 2) of each element were exposed at 5000° K. through a continuous wedge of 0.30 gradient. Other two samples (Sample 3 and 4) of each element were not exposed. Samples 1 and 3 of each element were stored in a freezer at −18° C., while samples 2 and 4 were stored at 24° C. and 50% relative humidity.

After four months of storing as described above, samples 3 and 4 of each element were exposed as said above, then all the samples (1, 2, 3 and 4 of each element, all exposed) were processed in a C-41 process as described in British Journal of Photography, July 1974, pages, 597-598.

The sensitometric results (fog and maximum density) and the relative speed of each sample, measured at 0.20 (Speed 1) above fog, are reported in the Table below.

In each element, the greater is the loss of relative speed of sample 2 with respect to samples 1 and 4, the greater is the amount of latent image fading; moreover, the greater the loss of speed of sample 4 with respect to sample 3, the greater the instability of the unexposed element.

TABLE 2

| Element | Sample | Fog | D. Max | Speed 1 |
|---|---|---|---|---|
| 4 | 4 | 0.11 | 2.40 | 96 |
| (Control) | 3 | 0.10 | 2.43 | 100 |
| | 2 | 0.11 | 2.38 | 78 |
| | 1 | 0.09 | 2.44 | 99 |
| 5 | 4 | 0.10 | 2.50 | 104 |
| (Invention) | 3 | 0.09 | 2.53 | 105 |
| | 2 | 0.09 | 2.49 | 107 |
| | 1 | 0.09 | 2.50 | 105 |

It can be understood from these results that the compound of the present invention has excellent effects in substantially inhibiting latent image fading and improving the stability of the unexposed element. Moreover, comparing the same samples of the control element, the element of the present invention has increased relative speed.

We claim:

1. A photographic silver halide emulsion containing a latent image stabilizing amount of a 2-unsubstituted N-alkenyl-thiazolium salt compound having the formula:

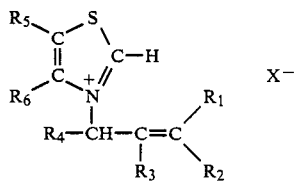

wherein $R_1$, $R_2$, $R_3$, $R_4$, $R_5$ and $R_6$ each represent a hydrogen atom or a photographically compatible substituent and $X^-$ represents an anion, and if $R_5$ and $R_6$ are combined they may only form a 5- or 6-membered non-aromatic ring.

2. The photographic silver halide emulsion of claim 1 wherein $R_1$, $R_2$, $R_3$ and $R_4$ each a hydrogen atom or an alkyl group and $R_5$ and $R_6$ each represent a hdyrogen atom, an alkyl group, an alkoxy group, an electron withdrawing group or can combine to form a 5- or 6-membered non-aromatic ring.

3. The photographic silver halide emulsion of claim 1 wherein said 2-unsubstituted N-alkenyl-thiazolium salt compound is present in said silver halide emulsion in an amount of from about 0.01 to about 50 millimoles per mole of silver.

4. A photographic element including a support bearing one or more silver halide emulsion layers, wherein at least one of said emulsion layers comprises a silver halide emulsion of claim 1.

5. A photographic element for use in color photography including a support bearing at least one blue-sensitive silver halide emulsion layer associated with a yellow dye-forming coupler, at least one green sensitive silver halide emulsion layer associated with a magenta dye-forming coupler and at least one red sensitive silver halide emulsion layer associated with a cyan dye-forming coupler, wherein at least one silver halide emulsion layer contains a latent image stabilizing amount of a 2-unsubstituted N-alkenyl-thiazolilum salt compound having the formula:

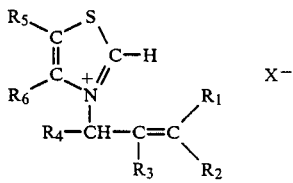

wherein $R_1$, $R_2$, $R_3$, $R_4$, $R_5$ and $R_6$ each represent a hydrogen atom or a photographically compatible substituent and $X^-$ represents an anion, and if $R_5$ and $R_6$ are combined they may only form a 5- or 6-membered non-aromatic ring.

6. The photographic element of claim 5 wherein $R_1$, $R_2$, $R_3$ and $R_4$ each represent a hydrogen atom.

7. The emulsion of claim 2 wherein $R_5$ and $R_6$ represent a hydrogen atom, alkyl group, alkoxy group or electron withdrawing group.

8. The emulsion of claim 3 wherein $R_5$ and $R_6$ represent a hydrogen atom, alkyl group, alkoxy group or electron withdrawing group.

9. The element of claim 5 wherein $R^5$ and $R^6$ represent a hydrogen atom, alkyl group, alkoxy group or electron withdrawing group.

10. The emulsion of claim 1 wherein $R_1$, $R_2$, $R_3$, and $R_4$ are hydrogen.

11. The emulsion of claim 2 wherein $R_1$, $R_2$, $R_3$ and $R_4$ are hydrogen.

12. The emulsion of claim 7 wherein $R_1$, $R_2$, $R_3$ and $R_4$ are hydrogen.

13. The emulsion of claim 8 wherein $R_1$, $R_2$, $R_3$ and $R_4$ are hydrogen.

14. The element of claim 9 wherein $R_1$, $R_2$, $R_3$ and $R_4$ are hydrogen.

15. The emulsion of claim 3 wherein $R_1$, $R_2$, $R_3$ and $R_4$ are hydrogen and $R_5$ and $R_6$ are hydrogen, alkyl, or alkoxy.

16. The element of claim 5 wherein $R_1$, $R_2$, $R_3$ and $R_4$ are hydrogen and $R_5$ and $R_6$ are hydrogen, alkyl, or alkoxy.

* * * * *

UNITED STATES PATENT AND TRADEMARK OFFICE
CERTIFICATE OF CORRECTION

PATENT NO. : 4,780,400

DATED : October 25, 1988

INVENTOR(S) : Beltramini and Squarcia

It is certified that error appears in the above-identified patent and that said Letters Patent is hereby corrected as shown below:

Column 3, line 53 "beng" should be --being--.

Column 5, line 4 "examle" should be --example--.

Column 5, line 4 "pyrazolotrizone" should be --pyrazolotrizole--.

Column 6, line 10 "0.24 " should be --0.23 --.

Signed and Sealed this

Seventh Day of November, 1989

Attest:

JEFFREY M. SAMUELS

*Attesting Officer*   *Acting Commissioner of Patents and Trademarks*